United States Patent [19]

Lam et al.

[11] Patent Number: 4,525,672
[45] Date of Patent: Jun. 25, 1985

[54] APPARATUS AND METHOD FOR LASER PUMPING OF NUCLEAR MAGNETIC RESONANCE CELL

[75] Inventors: Leo K. Lam, Canoga Park; Edward Phillips, Woodland Hills, both of Calif.

[73] Assignee: Litton Systems, Inc., Beverly Hills, Calif.

[21] Appl. No.: 480,608

[22] Filed: Mar. 30, 1983

[51] Int. Cl.³ ............................................. G01R 33/08
[52] U.S. Cl. ...................................... 324/304; 324/301
[58] Field of Search ................ 324/300, 301, 302, 304

[56] References Cited

U.S. PATENT DOCUMENTS 4,327,327 4/1982 Greenwood ........................ 324/304
4,430,616 2/1984 Grover ............................... 324/304

Primary Examiner—Michael J. Tokar
Attorney, Agent, or Firm—Elliott N. Kramsky

[57] ABSTRACT

A method and apparatus for optical pumping of an NMR cell by means of laser light. A current driver provides an a.c. current waveform as injection current to a laser diode. The resulting laser intensity spectrum closely approximates the absorption spectrum of the cell to thereby increase the signal generated for a given power input.

7 Claims, 5 Drawing Figures

APPARATUS AND METHOD FOR LASER PUMPING OF NUCLEAR MAGNETIC RESONANCE CELL

BACKGROUND OF THE INVENTION

1. Field of the Invention

The present invention relates to apparatus and a method for generating nuclear magnetic resonance. More particularly, this invention pertains to improved optical pumping of a nuclear magnetic resonance cell.

2. Description of the Prior Art

The utilization of nuclear magnetic resonance (hereinafter referred to as "NMR") in a gyroscope is disclosed in U.S. Pat. No. 4,157,495 which issued June 5, 1979 and which is assigned to the same assignee as the present invention.

The gyroscope disclosed therein operates on the principle of sensing inertial angular rotation rate or angular displacement about a sensitive axis as a shift in the Larmor precession frequency or phase, respectively, of one or more isotopes that possess nuclear magnetic moments.

The gyroscope is composed of an angular rotation sensor and associated electronics. The principal elements of the sensor are a light source, an NMR cell, a photodetector, a set of magnetic shields and a set of magnetic field coils. The principal elements of the electronics are signal processing circuits for extracting the Larmor precession frequency and phase information as well as circuits for generating and controlling various magnetic fields, both steady and varying sinusoidally with time, that are necessary for the proper operation of the device.

The NMR cell is mounted within a set of magnetic shields in order to attenuate external magnetic fields to acceptable low levels. Magnetic field coils are used to apply uniform magnetic fields to the NMR cell. Both a steady field and an a.c. carrier field are applied along the sensitive axis of the device and an a.c. feedback field is applied along one of the transverse axes. The d.c. magnetic fields along both transverse axes are controlled to be substantially zero. The NMR cell contains a single alkali metal vapor, such as rubidium, together with two isotopes of one or more noble gases, such as krypton or xenon. One or more buffer gases such as helium or nitrogen may also be contained in the cell.

As disclosed in the patent, the NMR cell is illuminated by a beam of circularly polarized light that originates from a rubidium lamp and thereafter passes through the cell at an angle with respect to the steady magnetic field. Absorption of some of this light causes the atomic magnetic moments of the rubidium atoms to be partly aligned in the direction of the steady magnetic field. This alignment is partly transferred to the nuclear magnetic moments of the noble gases, and these moments are caused to precess about the direction of the steady magnetic field, which, in turn, creates magnetic fields that rotate at the respective Larmor precession frequencies of the two noble gases. These rotating fields modulate the precessional motions of the rubidium magnetic moments, which in turn produce corresponding modulations of the transmitted light, thereby making it possible to detect the Larmor precession frequencies of the two noble gases optically.

The modulations of the light intensity are converted into electrical signals by a photodetector, and these signals are then electronically demodulated and filtered to provide signals at the Larmor precession frequencies of the two noble gases. The difference between the two precession frequencies is used to control the steady magnetic field so that it is substantially constant. One of the noble gas precession frequencies is subtracted from a precision reference frequency and the resulting difference frequency serves as a measure of the angular rotation rate of the gyroscope. The magnitude of an individual nuclear magnetic moment is extremely small, the natural equilibrium condition being one in which a nearly random orientation of moments exists in an ensemble of atoms. Techniques are employed to orient a significant fraction of such magnetic moments in a single direction so that a macroscopic magnetic moment, and consequently a measurable signal, will be produced.

The aligned magnetic moments of the single alkali metal system and of both noble gas systems of atoms are subject to relaxation mechanisms tending to cause their alignment to decay with time toward a random equilibrium orientation. Each system of moments is characterized by an individual relaxation time constant that depends upon the kinds and quantities of all constituents and upon the total environment within the cell. The steady state fractional alignment of each system of moments is a function of both the optical pumping rate and the relaxation time for the system.

The r.f.-powered alkali metal vapor lamp utilized for optical pumping and magnetometric detection in an NMR gyroscope of the type described above, when properly tuned, produces an output frequency spectrum that closely approximates the absorption spectrum of the rubidium vapor within the NMR cell. Such matching of spectra is inherent in the use of the same alkali metal vapor as both an emission medium and as an absorption medium.

While the r.f.-powered alkali metal vapor lamp has provided acceptable optical pumping of the NMR cell, this type of light source is characterized by a relatively large size, weight and power consumption. Such characteristics have, in fact, rendered the NMR gyroscope unsuitable for some applications and have rendered the device only marginally effective in others.

One optical source that possesses favorable operational characteristics vis a vis the vapor lamp in the areas of size, weight and power consumption is the laser diode. In addition to the relative savings in space and power requirements effected by such device, the use of laser light introduces the advantage of frequency tunability and high beam collimation into the optical pumping process.

A disadvantage associated with the use of laser, as opposed to vapor lamp, light results from its inherently narrow bandwidth. While a highly advantageous property for many applications, the narrow bandwidth of laser emissions limits the amount of NMR signal that can be generated by failing to utilize a significant portion of the absorption spectrum of the rubidium (or other alkali metal) vapor within the NMR cell.

SUMMARY OF THE INVENTION

The present invention addresses and resolves the aforesaid and additional problems of the prior art by providing, in a first aspect, a method for optically pumping an NMR cell. The method includes the steps of directing a beam of circularly polarized light at the cell and varying the spectral profile of the laser light to approximate the absorption profile of the cell.

In a second aspect, the invention comprises apparatus for optically pumping an NMR cell. Such apparatus comprises the combination of a laser diode and means for modulating the diode so that the spectral profile of the laser light emitted therefrom approximates the absorption profile of the cell.

The foregoing and additional features and advantages of the invention will become apparent from the detailed description which follows in conjunction with the set of drawing figures. In the figures and in the detailed description numerals are utilized corresponding to the invention's features, like numerals of the figures and detailed description corresponding to like features of the invention throughout.

DETAILED DESCRIPTION

Figure 1:
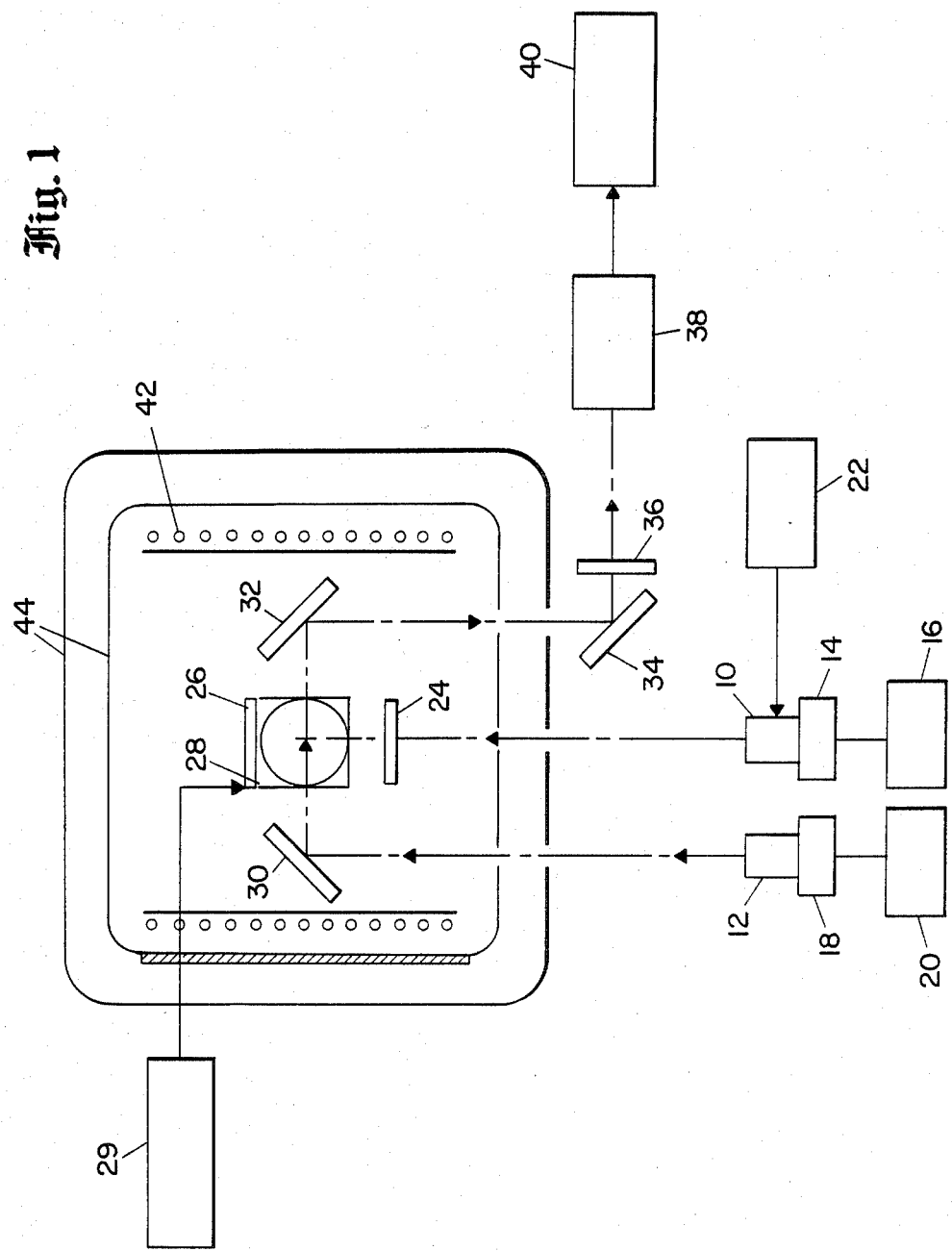
FIG. 1 is a schematic view of an NMR rotation sensor incorporating optical pumping apparatus in accordance with the invention.

FIG. 1 presents a schematic view of a rotation sensor or gyroscope of the NMR type configured and employing optical pumping in accordance with the present invention. In the gyroscope, laser light, as opposed to that output from an alkali vapor lamp, is utilized for effectuating both the generation of angular momentum (i.e. optical pumping) and the signal detection process.

The system includes laser diodes 10, 12, for effectuating the pumping and detection processes, respectively. In an actual embodiment of the system laser diodes commercially available from the Mitsubishi Corporation under part number ML 4001-5340 were employed for both processes. The operating temperatures of these temperature-sensitive lasers are regulated by thermoelectric heater/coolers 14, 18 under the control of temperature control units 16 and 20 respectively. A laser diode current driver 22 provides injection current for controlling the output of the laser 10. (The laser 12 is also actuated by a unit that provides an injection current thereto (not shown); however, the laser diode current driver 22, unlike the unit associated with the laser diode 12, includes conventional wave-shaping and timing circuitry for modulating the current output of a power supply associated therewith in accordance with the invention.) As will be seen below, the output current of the driver 22 modulates the frequency spectrum of the laser 10 to enhance the system performance.

The beam of light emitted from the laser 10 strikes a circular polarizer 24 which may be a quarter wave plate. After passing through the polarizer 24, it enters an NMR cell 26. Certain atomic and electronic interactions which occur within the cell 26 in response to the laser light that are essential to the operation of NMR apparatus, are discussed below with reference to FIG. 2. The temperature of the elements within the NMR cell 26 is carefully controlled by means of a heater/cooler 28 in conjunction with a temperature control unit 29. Magnetic field coils 42 establish a local magnetic field about the cell 26 while a double layer of magnetic shielding 44 acts to attenuate the effects of external magnetic fields.

The laser beam emergent from the diode 12 is directed through the NMR cell 26 in a direction transverse to the beam from the diode 10 and is subsequently directed to opto-electronic detection circuitry by the indicated arrangement of mirrors 30, 32 and 34. As is well known in the art, the precessing NMR field created within the cell 26 modulates the optical activity of the rubidium vapor therein; hence the beam from the diode 12, after passing through the cell 26, is optically modulated to reflect such activity.

After reflection by the mirror 34, the detection beam passes through an output polarizer 36 that lowers the (essentially photon quanta limited) noise within the beam. The output beam's intensity is transformed into an electronic signal upon striking a conventional silicon photodetector 38 and the desired rotation data derived therefrom by means of appropriate signal processing electronics 40.

Figure 2:
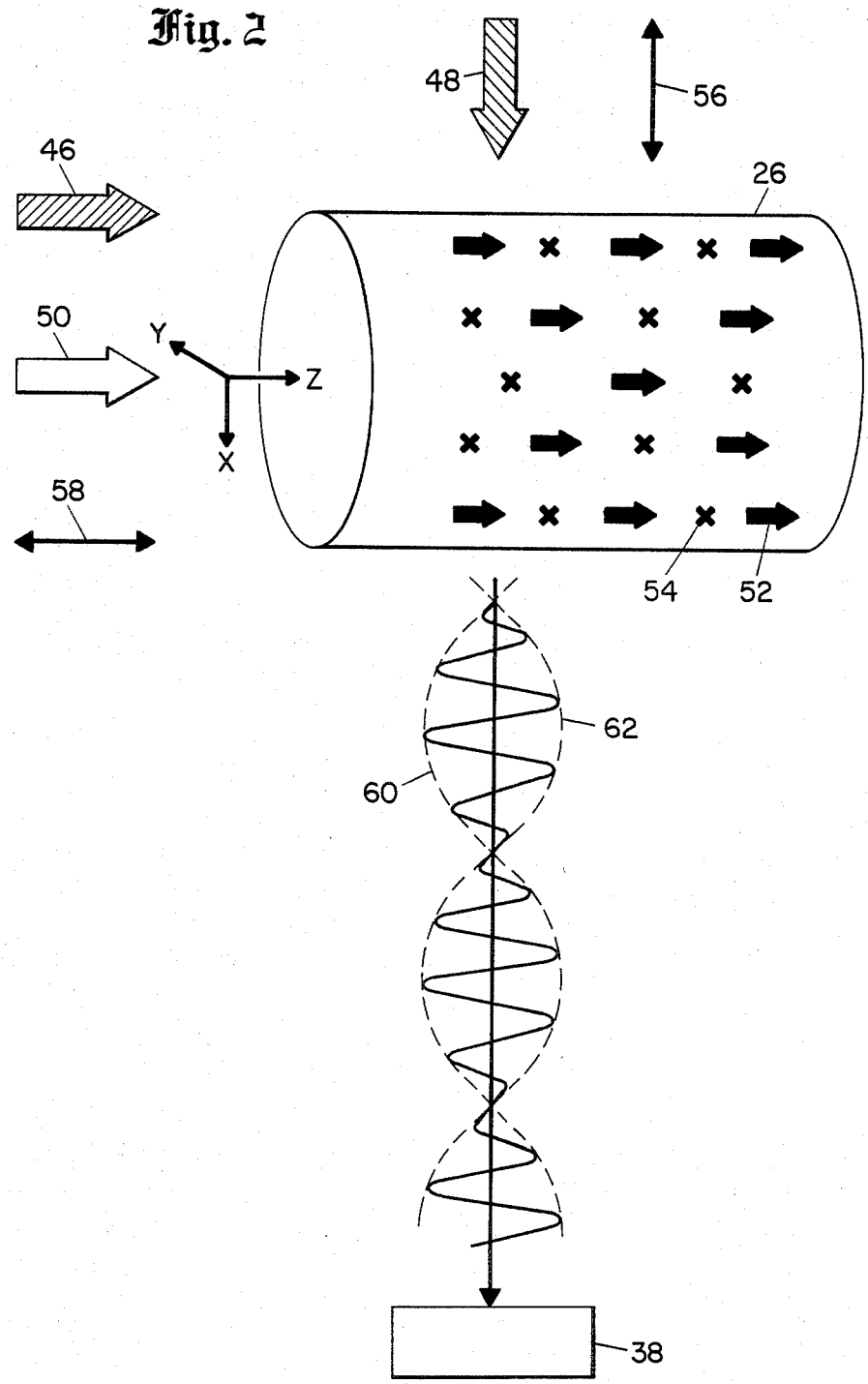
FIG. 2 is a functional schematic view of an NMR cell for the purpose of illustrating a laser optical pumping process in accordance with the invention.

FIG. 2 is a conceptual diagram illustrating, for each of the noble gases within the cell 26, the processes of optical pumping and modulation of the intensity of the light that is transmitted through the cell. Because these processes are so similar for both noble gases employed, they are illustrated and described for only one of these gases. The circularly polarized pumping light 46, which enters the NMR cell 26, is directed along the indicated z-axis, and detection light 48 from the laser diode 12 is directed along the indicated x-axis. Through the interactions of the optical pumping light 46 and a steady magnetic field 50, generated by the coils 42 (shown in FIG. 1), the magnetic moments of rubidium atoms 52 become preferentially aligned in the z-direction. This magnetic moment alignment is then transferred from the rubidium atoms 52 to the noble gas nuclei 54 in a spin exchange process.

A sinusoidal a.c. feedback magnetic field 56, matched in frequency and phase to the Larmor precession frequency of the collective magnetic moment of the noble gas nuclei 54, is applied along the x-direction and serves to torque the magnetic moment of the nuclei to the x-y plane. This component of noble gas nuclear magnetic moment will then precess within the x-y plane about the steady magnetic field 50 at the noble gas Larmor precession frequency. The precessing nuclear magnetic moment creates a nuclear precession magnetic field of strength, $h_a$, that rotates in the x-y plane with a component in the y-direction that is equal to ($h_a \cos \omega_a t$).

The detection light 48 interacts with the rubidium atoms 52, which are under the influence of the steady magnetic field 50, a superimposed a.c. carrier magnetic field 58, and the y-component of the nuclear precession field $h_a$. This interaction causes the intensity of the x-component of the transmitted light 60 to be modulated at the carrier frequency $\omega_c$. This modulated light is then converted into electrical signals by the silicon photodetector 38.

Figure 3:
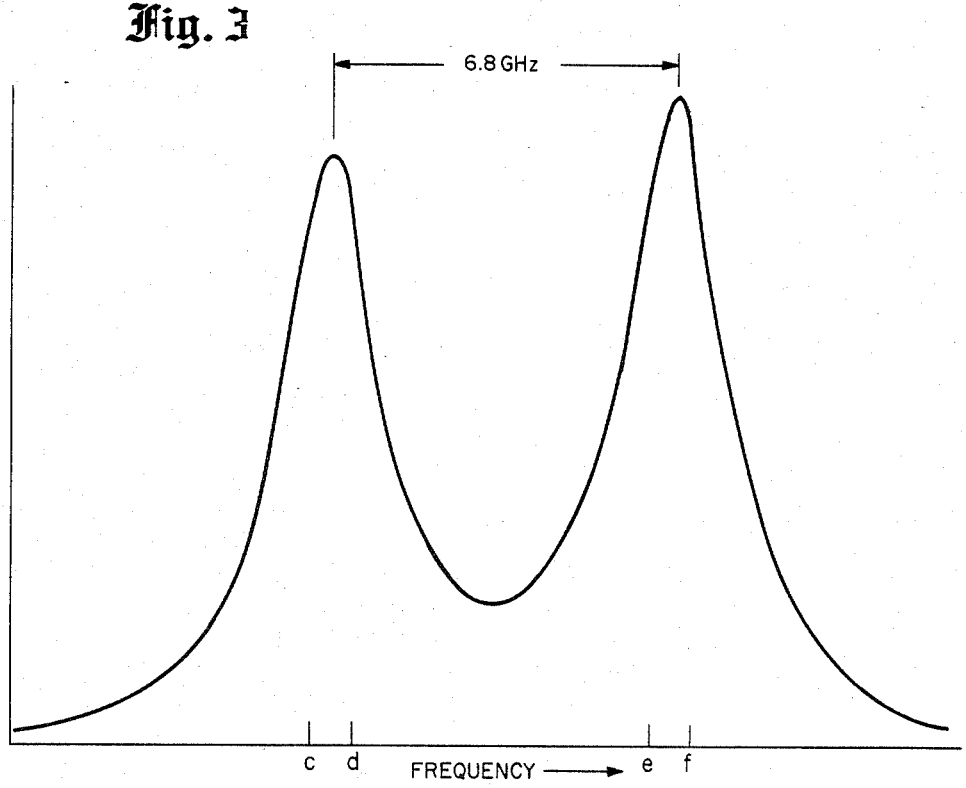
FIG. 3 is a graphical representation of the D1 absorption spectrum of rubidium.

FIG. 3 is a graph of the measured absorption spectrum for the D1 transition (which can occur in the frequency range of laser light) of Rb 87 vapor in a RbXe NMR cell. The cell, in addition to 10 to 20 micrograms of purified Rb 87 metal, also included approximately one half Torr of Xe 129, two Torr of Xe 131, 100 Torr of helium and 40 Torr of nitrogen gas. Lines lettered "c", "d", "e" and "f" indicate the hyperfine structure of the D1 transition. The cell was maintained at 80 degrees Celsius, and the resulting absorption spectrum consists of two broad components with an approximate peak-to-peak frequency separation of 6.8 GHz. The form of the absorption curve reflects the various effects of Doppler, temperature, pressure and collision broadening and presents a statistical measure of the likelihood of a D1 transition taking place in response to the application of a range of wavelengths of energy to the NMR cell.

Radiation of various wavelengths (and frequencies) corresponds to differing energy levels. Circularly polarized radiation, such as the optical beam from the laser diode 10, when absorbed, effects not only a change in the energy state of the rubidium vapor but also a net change in the angular momentum of the rubidium atoms. This net change in angular momentum, necessary for the successful operation of an NMR gyroscope, reflects the differential population of the various atomic states that, in accordance with quantum theory, describe a given rubidium atom.

As is implicit in the curve of FIG. 3, a range of frequencies of laser energy may be absorbed by the NMR cell, and, as disclosed above, such absorption will, in part, increase the angular momentum of the rubidium atoms. Such angular momentum, as mentioned above, is then transferred to the nuclei of the noble gas within the cell that may then be made to precess in a local magnetic field, producing an output signal.

Figure 4:
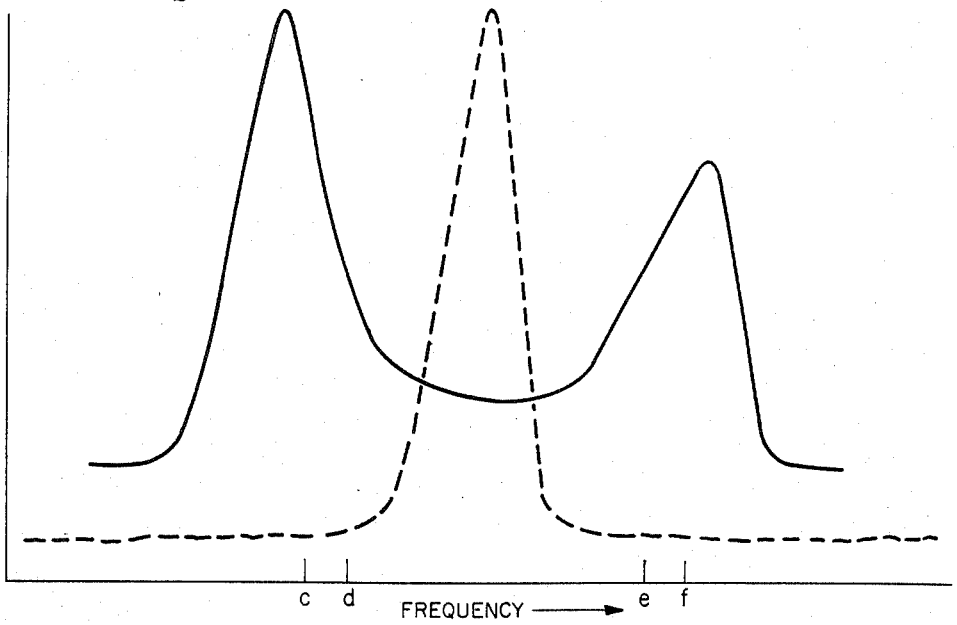
FIG. 4 is a graph of the output spectra produced by an ML4001-5340 laser diode driven by injection currents modulated in accordance with the invention and not so modulated.

FIG. 4 is a graph of the output spectra (intensity versus wavelength) produced by an ML 4001-5340 laser diode driven by injection currents modulated in accordance with the invention (solid line) and not so modulated (dashed line). The solid curve was driven by a 10 kiloHertz square wave current from the laser diode current driver 22 of 2.8 milliamps peak-to-peak and d.c. value of 21 milliamps. The laser diode 10 was, for the particular curve shown in FIG. 4, maintained at 24° Celsius by the heater/cooler 14 and temperature control 16. As can be seen, the resulting output spectrum of the laser diode 10 is significantly altered in comparison to its output when driven purely by d.c. Thus, the output of a laser diode modulated in accordance with the invention will produce a double-peaked intensity spectrum for a given power input. Referring back to the preceding figure, it can be seen that the intensity of the laser output is spread over a frequency range as a result of the use of a.c. modulated injection current to more closely coincide with the absorption spectrum of the NMR cell than does the output spectrum of a laser diode driven by purely d.c. injection current. Comparing the two curves of FIG. 4, the dashed output of the purely d.c. driven diode indicates a relative concentration of laser energy into a narrow spectrum which can at best be tuned to coincide with only one of the two peaks of the absorption spectrum of the NMR cell. This is in contrast to the shape of the laser output spectrum driven by a.c. modulated injection current which can be seen to more closely approximate the shape of the absorption spectrum.

As a result of the substantially improved matching of laser emission spectrum to rubidium absorption spectrum, it is apparent that, by modulating laser output in accordance with the invention, a greater amount of the energy produced by the laser will be absorbed by the atoms and electrons in the cell, increasing the amount of angular momentum imparted to the rubidium atoms and therefore the amount of signal produced by the overall system.

A comparable increase in the absorption of the laser light could be achieved by increasing the cell temperature and hence the Rb density. This method would shorten the transverse relaxation time of the noble gas nuclear moment and hence degrade the gyro performance. The present method is particularly important in the case of low Rb vapor density, when the laser diode pumping rate greatly exceeds the Rb-Rb spin exchange rate, a condition that applies in the Rb-Xe NMR gyroscope. By shaping the time-averaged emission line profile to match the absorption profile, more efficient pumping is achieved without degradation of the noble gas nuclear moment precession.

In providing an injection current in accordance with the invention, the a.c. current must oscillate with such frequency that its period of oscillation does not exceed the relaxation time constant of the rubidium atoms. By so choosing the modulating waveform, advantage is taken of the shape of absorption profile of the NMR cell. If the period of the oscillations of the modulating current, and the resulting periods of intensity of the two distinct (though broadened) output wavelengths resulting therefrom, were to exceed the rubidium relaxation time constant, the time-averaged effect of a double-peaked laser profile would disappear, depriving the pumping system of the above described advantages of the double-peaked broadened output intensity spectrum of the solid curve that more closely matches the absorption spectrum of the NMR cell.

Figure 5:
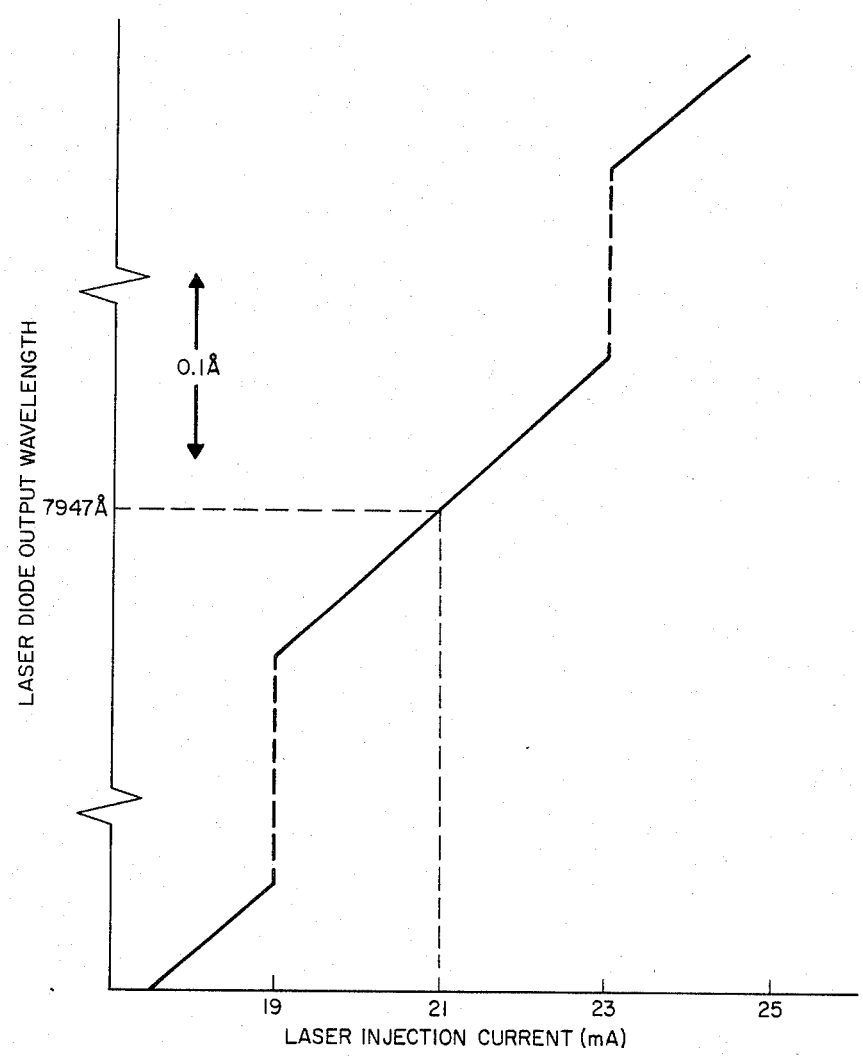
FIG. 5 is a graphical representation of the wavelength versus-injection current characteristic for the ML 4001-5340 laser diode.

FIG. 5 is a graph of output wavelength versus injection current for an ML 4001-5340 laser diode operating at 23 degrees Celsius. As can be seen, the curve evidences a series of ranges of linear response and illustrates the choice of an operating point about which the output laser frequency can be smoothly and continuously modulated over a range of 6.8 GHz.

Applicants have found that, by proper choice of laser modulating current waveform, an output spectrum can be generated in accordance with that shown in FIG. 4. The particular square wave chosen was selected by oscillation of the current about a d.c. value corresponding to the mean wavelength of the D1 hyperfine structure (i.e. average wavelength of c, d, e and f lines). As mentioned above, the frequency of the a.c. component of the waveform is chosen so that rubidium relaxation time constant will not be exceeded by the period of the waveform and peak-to-peak values of the driving current are selected so that the humps of the laser output generally coincide with the humps of the rubidium absorption spectrum.

While the invention has been described with reference to its preferred embodiment, it is by no means limited thereto. Numerous variations are intended to fall within the teaching herein, as defined in the appended claims, including, but not limited to, the substitution of comparable elements and devices to those disclosed herein, the adjustment of the duty cycle of the modulating waveform to produce unequal peak heights in the double peak profile, and the use of laser-modulating a.c. current waveforms to improve the matching of laser output with NMR absorption spectra.

What is claimed is:

1. A method for optically pumping an NMR cell of the type wherein an a.c. magnetic field torques the collective magnetic moment of the noble gas nuclei comprising the steps of:

(a) directing a beam of circularly polarized laser light at said cell; and (b) shaping the spectral profile of said laser light to approximate the absorption profile of said cell.

2. A method as defined in claim 1 wherein the step of varying the spectral profile of said laser light includes the step of modulating a laser diode by driving said diode with a preselected a.c. current waveform so that the spectral profile of the output laser light approximates the cell absorption profile.

3. A method as defined in claim 2 wherein said preselected a.c. waveform is a square wave having d.c. value corresponding to the mean wavelength of the hyperfine components of the absorption spectrum of the cell.

4. Apparatus for optically pumping an NMR cell comprising, in combination:

(a) a laser diode; and (b) means for shaping the output of said diode so that the spectral profile of the laser light emitted therefrom closely approximates the absorption profile of said cell and (c) means for applying an a.c. magnetic field matched in phase and frequency to the collective magnetic moment of the noble gas nuclei.

5. Apparatus as defined in claim 4 wherein said means includes means for providing an a.c. current waveform having a d.c. value corresponding to the mean wavelength of the hyperfine components of the cell absorption spectrum.

6. Apparatus as defined in claim 5 wherein said laser diode is of the CW single mode type.

7. Apparatus as defined in claim 6 wherein said laser is a GaAlAs diode laser.

* * * * *